United States Patent [19]

Felix

[11] Patent Number: 5,234,895

[45] Date of Patent: Aug. 10, 1993

[54] ARYLPYRIDONE HERBICIDES

[75] Inventor: Raymond A. Felix, Richmond, Calif.

[73] Assignee: Imperial Chemical Industries PLC, London, United Kingdom

[21] Appl. No.: 901,008

[22] Filed: Jun. 19, 1992

[51] Int. Cl.$^5$ ............... C07D 211/40; C07D 211/74; C07D 211/80; A01N 43/40
[52] U.S. Cl. .................... 504/254; 504/255; 546/214; 546/216; 546/221; 546/283; 546/290; 546/300; 546/301; 546/302
[58] Field of Search ............... 546/214, 216, 221, 290, 546/301, 303, 283, 300; 514/327, 345; 504/254, 255

[56] References Cited

U.S. PATENT DOCUMENTS 4,051,142 9/1977 Carlson ..................... 546/288
4,152,136 5/1979 Taylor ..................... 546/283

Primary Examiner—C. Warren Ivy
Assistant Examiner—Celia Chang
Attorney, Agent, or Firm—Joel G. Ackerman

[57] ABSTRACT

Compounds having the formula

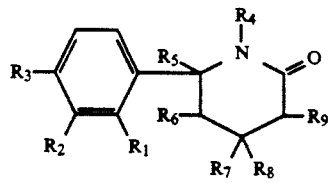

in which:
- $R_1$ is hydrogen or fluoro;
- $R_2$ is halo, trihalomethyl, pentahaloethyl, mono- or difluoromethyl, di-, tri- or tetrafluoroethyl, $C_1$-$C_2$ fluoroalkylthio, $C_1$-$C_2$ fluoroalkoxy, methylthio, methylsulfonyl, halomethylsulfonyl, $C_1$-$C_2$ alkyl or methoxy;
- $R_3$ is hydrogen or halo;
- $R_4$ is hydrogen, $C_1$-$C_4$ alkyl; $C_2$-$C_4$ alkenyl; $C_2$-$C_4$ alkynyl; $C_1$-$C_4$ haloalkyl; $C_2$-$C_4$ haloalkenyl; $C_1$-$C_4$ alkoxy; $C_2$-$C_4$ alkoxyalkyl, 3-trifluoromethylphenyl, or —$(CH_2)_nY$;
- $R_5$ and $R_6$ are hydrogen, or $R_5$ and $R_6$ together form a bond;
- $R_7$ is $C_1$-$C_4$ alkyl;
- $R_8$ and $R_9$ are hydrogen, or $R_8$ and $R_9$ together form a bond;
- Y is cyano; 4-chlorophenyl; $C_3$-$C_6$ cycloalkyl, furyl or tetrahydrofuryl optionally substituted by halo or $C_1$-$C_4$ alkyl; or $COR_{10}$ in which $R_{10}$ is hydroxy, $C_1$-$C_5$ alkoxy, $C_1$-$C_5$ alkylthio, —$OCH_2COO(C_1$-$C_4$ alkyl) or $NR_{11}R_{12}$ in which $R_{11}$ and $R_{12}$ are independently hydrogen, $C_1$-$C_4$ alkyl, $C_1$-$C_6$ alkoxy, or $C_2$-$C_4$ alkoxyalkyl; and
- n is 1 or 2 are herbicides.

27 Claims, No Drawings

ARYLPYRIDONE HERBICIDES

FIELD OF THE INVENTION

This invention relates to certain arylpyridone compounds which demonstrate herbicidal activity.

DESCRIPTION OF THE INVENTION

According to this invention, compounds of the following structure have been found to exhibit herbicidal activity:

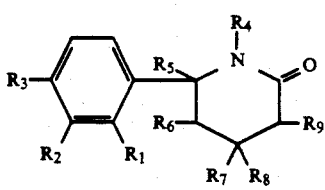

in which:

$R_1$ is hydrogen or fluoro;

$R_2$ is halo, trihalomethyl, pentahaloethyl, mono- or difluoromethyl, di-, tri- or tetrafluoroethyl, $C_1$-$C_2$ fluoroalkylthio, $C_1$-$C_2$ fluoroalkoxy, methylthio, methylsulfonyl, halomethylsulfonyl, $C_1$-$C_2$ alkyl or methoxy;

$R_3$ is hydrogen or halo;

$R_4$ is hydrogen, $C_1$-$C_4$ alkyl; $C_2$-$C_4$ alkenyl; $C_2$-$C_4$ alkynyl; $C_1$-$C_4$ haloalkyl; $C_2$-$C_4$ haloalkenyl; $C_1$-$C_4$ alkoxy; $C_2$-$C_4$ alkoxyalkyl, 3-trifluoromethylphenyl, or —$(CH_2)_nY$;

$R_5$ and $R_6$ are hydrogen, or $R_5$ and $R_6$ together form a bond;

$R_7$ is $C_1$-$C_4$ alkyl;

$R_8$ and $R_9$ are hydrogen, or $R_8$ and $R_9$ together form a bond;

Y is cyano; 4-chlorophenyl; $C_3$-$C_6$ cycloalkyl, furyl or tetrahydrofuryl optionally substituted by halo or $C_1$-$C_4$ alkyl; or $COR_{10}$ in which $R_{10}$ is hydroxy, $C_1$-$C_5$ alkoxy, $C_1$-$C_5$ alkylthio, —$OCH_2COO(C_1$-$C_4$ alkyl) or $NR_{11}R_{12}$ in which $R_{11}$ and $R_{12}$ are independently hydrogen, $C_1$-$C_4$ alkyl, $C_1$-$C_6$ alkoxy, or $C_2$-$C_4$ alkoxyalkyl; and n is 1 or 2.

The terms "alkyl", "alkenyl" and "alkynyl" include both straight and branched chain groups having the indicated number of carbon atoms. "Halo" includes chloro, fluoro, bromo and iodo.

Preferred groups are:

For $R_2$: chloro, fluoro, bromo, trifluoromethyl, trifluoromethylthio, trifluoromethoxy, methyl and methoxy;

For $R_4$: $C_1$-$C_4$ alkyl; $C_1$-$C_4$ alkoxy; $C_1$-$C_4$ haloalkyl; cyanomethyl $C_2$-$C_4$ alkenyl; $C_2$-$C_6$ alkoxyalkyl; $C_2$-$C_4$ alkynyl; $C_2$-$C_4$ haloalkenyl; ($C_3$-$C_6$ cycloalkyl)methyl; furylmethyl; tetrahydrofurylmethyl or

in which $R_{10}$ is hydroxy, $C_1$-$C_5$ alkoxy, $NH_2$ or $N(C_1$-$C_4$ alkyl)$_2$;; and For $R_7$: methyl.

The compounds of this invention include pyridones ($R_5$ and $R_6$, and $R_8$ and $R_9$ together form bonds), dihydropyridones ($R_5$ and $R_6$ form a bond and $R_8$ and $R_9$ are both hydrogen), and piperidones or tetrahydropyridones ($R_5$, $R_6$, $R_8$ and $R_9$ are all hydrogen).

As used herein, the term "herbicide" means a compound or composition which adversely controls or modifies the growth of plants. By the term "herbicidally effective amount" is meant any amount of such compound or composition which causes an adverse modifying effect upon the growth of plants. By "plants", it is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing, and the like.

The compounds of this invention have been found to be active herbicides, as pre- and/or post-emergent herbicides. Pre-emergence herbicides are applied prior to emergence of vegetation from the soil; post-emergence herbicides are applied to control or kill existing vegetation. Some of the compounds of this invention have demonstrated post-emergence herbicidal activity in a relatively short time, and against some weeds, with a very strong effect. Herbicides having such rapid and extensive post-emergence activity are sometimes referred to as "contact-and-burn" or "burn-down" herbicides and are used, among other applications, for clearing vegetation from land such as building lots, highway median strips, railroad track beds, and crop land prior to planting or in minimum till or no-till farming. Some of the compounds of this invention have demonstrated good to excellent control of nutsedge, a particularly difficult type of weed to control.

Compounds showing "contact-and-burn" effect, but little or no pre-emergence activity, may be useful in clearing land prior to planting since planting of a crop can be done relatively soon after the herbicide is applied.

Compounds of this invention in which $R_5$ and $R_6$ form a bond may be prepared according to the following process:

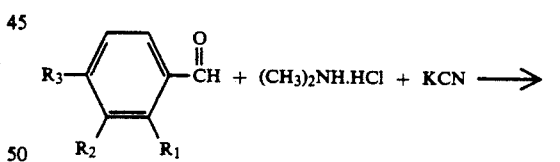

(1)

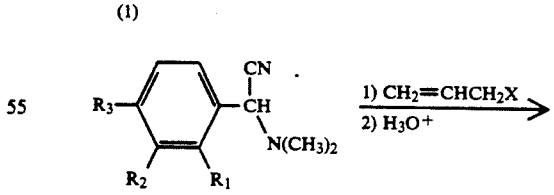

(2)

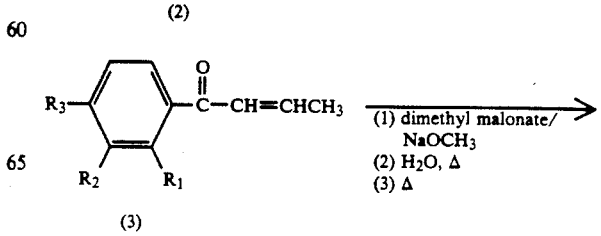

(3)

-continued

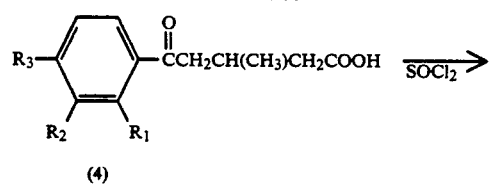

(4)

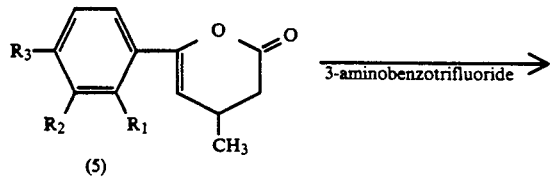

(5)

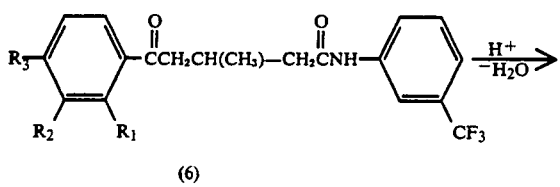

(6)

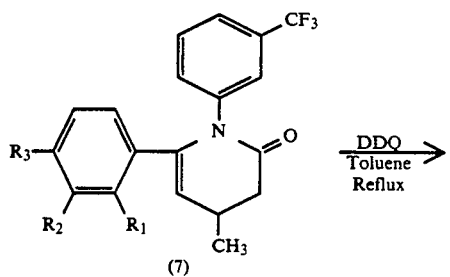

(7)

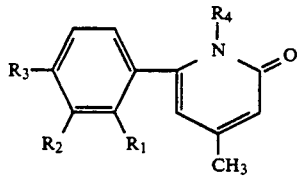

In this process, a benzaldehyde (1) is reacted with dimethylamine (e.g. as the hydrochloride) and potassium cyanide, and hen with an allyl halide to produce a phenylpropenyl ketone (3). The ketone is then reacted with dimethyl malonate, and the reaction product is hydrolyzed and then heated at about 160°–170° C. to form a keto acid (4). The keto acid is then cyclized, for example with thionyl chloride, to form a pyrone (5), which is then converted by reaction with 3-aminobenzotrifluoride and dehydration to the final dihydropyridone product.

The following are examples of the preparation of compounds of this invention.

EXAMPLE 1

Preparations of 1-(carboethoxy)methyl -3,4-dihydro-4-methyl 6-(3'-trifluoromethyl)phenyl -2-(1H)-pyridone (Compound 3)

a. To a solution of 33.75 g (0.55 mole) potassium cyanide in 150 ml water, there was added, dropwise, 66.9 ml (0.5 mole) m-trifluoromethylbenzaldehyde, with cooling in an ice bath. When all the benzaldehyde had been added, 57 g (0.7 mole) of dimethylamine hydrochloride in 147 ml water was added. The mixture was reacted in a closed system, with stirring, at 25° C. overnight. After workup with ether and water, there was obtained 100 3 g (88% of theoretical yield of 2-dimethylamino-2-(3'-trifluoromethyl)phenyl acetonitrile.

b. Product of Step (a) (52.3 g, 0.23 mole) was combined with 24.2 ml (0.28 mole) allyl bromide, 45 ml benzene, 91.6 ml 50% caustic solution and 2 g tetra-n-butylphosphonium bromide (phase trasfer catalyst). The mixture was heated to reflux for ½ hour. The contents were cooled, extracted with water and ether, and the solvents stripped. Then, 419 ml of 2N HCl was added to the residue, the mixture was refluxed for 1½ hour, cooled and extracted with water and ether. There was obtained 44.3 g of 1-(3-trifluoromethylphenyl)-but-2-enone.

c. Product of Step (b) (44.3 g, 0.207 mole) was combined with 4.7 ml (0.0207 mole) of 25% sodium methoxide (in methanol), 23.6 ml (0.207 mole) dimethyl malonate and 600 ml methanol. The mixture was stirred for 16 hours at room temperature. Then, there was added 49.7 g of 50% caustic solution and 49.7 ml water. The mixture was refluxed for one hour, methanol was stripped off, and the resulting mixture was extracted with water and ether. The aqueous phase was treated with concentrated HCl to reduce the pH to 1, then extracted with methylene chloride. There was obtained 50 g (77% of theoretical yield) of 2-carboxy-3-methyl-4-(3'-trifluoromethyl)benzoyl butyric acid.

d. The product of Step (c) was heated in an oil bath to 160°–170° C. until gas evolution ceased. There was obtained 40.0 g (82% of theoretical yield) of 3-methyl-4-(3'-trifluoromethyl)benzoyl butyric acid.

e. Product from Step (d) (8.2 g, 0.03 mole) was combined with 9 ml thionyl chloride and 80 ml methylene chloride. The mixture was stirred for one hour (at room temperature and stripped. There was obtained 7.6 g (99% of theoretical yield) of 3,4-dihydro-4-methyl-6-[3'-trifluoromethyl)phenyl-1,2-pyrone.

f. The product of Step (e) (10.0 g, 0.039 mole) was combined with 6.1 g, (0.44 mole) of glycine ethyl ester hydrochloride in 125 ml methylene chloride. To the resulting mixture there was added 6.3 ml triethylamine, dropwise. The mixture was stirred overnight, then worked up with dilute HCl and dilute sodium bicarbonate. The residue was analyzed and dissolved in 120 ml benzene. A catalytic amount of methane sulfonic acid was added. The mixture was refluxed with azeotropic removal of water, and extracted with ether and dilute sodium bicarbonate. There was obtained 10.75 g (95% of theoretical yield) of the desired product.

EXAMPLE 2

Preparation of 1-(carboethoxy)methyl-4-methyl-6-(3'-trifluoromethyl)-phenyl-2-piperidone (Compound 25 herein)

Two grams (0.006 mole) of the product of Example 1 was combined with 11 g Raney nickel in 30 ml ethanol at room temperature, and the mixture was stirred for 1½ hours. Then, it was heated to reflux for ½ hour; the heat source was removed and 20 g additional Raney nickel was added. The mixture was stirred for 3½ hours at room temperature. Additional 12 g Raney nickel was added and the mixture stirred at room temperature for 64 hours at which point the reaction was determined to be over. The reaction product was filtered, stripped, dissolved in methylene chloride, dried over magnesium sulfate, and again filtered and stripped. There was obtained 1.6 g (78% of theoretical yield) of the desired product, whose identity was comfirmed by spectroscopic analyses.

EXAMPLE 3

Preparation of 1-(carboethoxy)methyl-4-methyl-6-(3-trifluoromethyl)-phenyl-2-1H)-pyridone (Compound 26 herein)

Two grams (0.006 mole) of the product of Example 1 was combined with 1.9 g (0.0084 mole) of dichlorodicyanobenzoquinone (DDQ) and 25 ml toluene. The mixture was refluxed for 1½ hours, cooled and treated with ether and water. Four grams of crude product was collected. The crude product was passed through a packed alumina column eluting with acetonitrile. There was recovered 1 g (49% of theoretical yield) of the desired product, whose identity was comfirmed by spectroscopic analyses.

Table I depicts representative compounds of this invention, prepared by a process as described above. Most compounds were obtained as oils. Structures were confirmed by spectroscopic analyses.

TABLE I

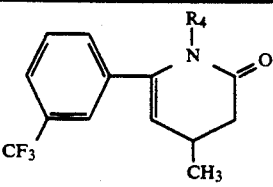

| Compound No. | $R^4$ |
|---|---|
| 1 | H |
| 2 | 3-CF$_3$C$_6$H$_4$ |
| 3 | —CH$_2$COOC$_2$H$_5$ |
| 4 | —CH$_2$CONH$_2$ |
| 5 | —CH$_2$CN |
| 6 | —CH$_2$CF$_3$ |
| 7 | —(CH$_2$)$_2$COOCH$_3$ |
| 8 | —CH$_2$COOH |
| 9 | —CH$_2$CON(CH$_3$)$_2$ |
| 10 | —CH$_2$COOCH$_2$COOCH$_3$ |
| 11 | —CH$_2$COO(t-C$_4$H$_9$) |
| 12 | —CH$_2$COO(i-C$_3$H$_7$) |
| 13 | —CH$_2$C(Cl)=CH$_2$ |
| 14 | —CH$_2$CH=CH$_2$ |
| 15 | —CH$_2$C≡CH |
| 16 | —CH$_2$—⌬—Cl |
| 17 | —(CH$_2$)$_2$OCH$_3$ |
| 18 | n-C$_3$H$_7$ |
| 19 | —CH$_2$CH=CHCl |
| 20 | —CH$_2$—(furanone) |
| 21 | —CH$_2$—(furanone) |
| 22 | —CH$_2$—△ |

TABLE I-continued

| Compound No. | $R^4$ |
|---|---|
| 23 | CH$_3$ |
| 24 | OC$_2$H$_5$ |

The following additional compounds within the scope of this invention have been prepared and these structures confirmed by analyses.

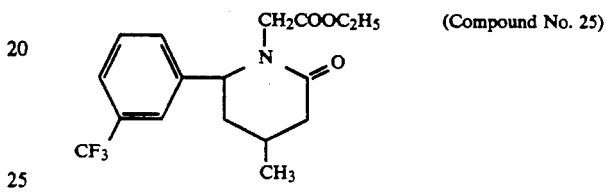
(Compound No. 25)

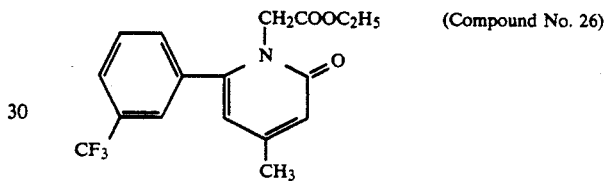
(Compound No. 26)

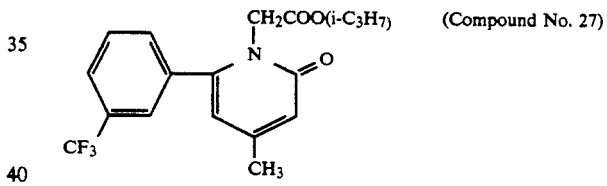
(Compound No. 27)

Herbicidal Activity Tests

Compounds 1–27 were tested for herbicidal activity as follows:

The herbicidal effect was observed by comparing the extent of weed control in test flats treated with the compounds against that occurring in similar non-treated control flats. All were applied at 3.57 lb/A (4 kg/ha) to pre-emergence and post-emergence screening flats. An 80 gal/A (748.3 l/ha) spray volume was utilized. Post-emergence flats were seeded 12 days prior to treatment. Pre-emergence flats were seeded one day prior to treatment. Overhead watering of pre-emergence flats and soil surface watering of post-emergence flats, so as to avoid wetting the foliage, were carried out for the duration of the test.

Weed seeds were planted in a flat at a seed depth of 0.5 inch (1.3 cm). Soil for flats was prepared using sandy loam soil fortified with 17-17-17 fertilizer (N-P$_2$O$_5$-K$_2$O on a weight basis) and Captan 80 W fungicide. The test weeds were as follows:

| COMMON NAME | SCIENTIFIC NAME |
|---|---|
| green foxtail | *Setaria viridis* |
| watergrass | *Echinochloa crus-galli* |
| wild oat | *Avena fatua* |

| -continued | |
|---|---|
| COMMON NAME | SCIENTIFIC NAME |
| annual morning glory | *Ipomoea purpurea* |
| velvetleaf | *Abutilon theophrasti* |
| wild mustard | *Sinapsis arvensis* |
| yellow nutsedge | *Cyperus esculentus* |

The spray solutions were prepared by dissolving 240 mg of test compound in 20 ml of acetone containing 1% polyoxyethylene sorbitan monolaurate emulsifier, then adding 20 ml of water to the resulting solution. The stock solutions were applied using a linear spray table. Pre-emergence flats are raised to the level of the post-emergence foliage canopy by setting the flats on a wooden block.

The degree of weed control was visually assessed and recorded as percentage control compared to the growth of the same species in an untreated check flat of the same age. The rating scale ranges from 0 to 100%, where 0 equals no effect with plant growth equal to the untreated control, and 100 equals complete kill.

Ratings were taken in pre-emergence tests approximately 15–18 days after treatment (DAT). In post-emergence tests, ratings were taken at two intervals. On the sixth day after treatment, overall control was rated, as an indication of total vegetative control, or "contact and burn" activity. Approximately 15–18 days after treatment, the tests were rated for overall post-emergence activity.

Results are listed in Table II below, expressed as average control of the three grasses (GR) (wild oat, watergrass, foxtail) and three broadleaf weeds (BL) (morningglory, mustard, velvetleaf), and of nutsedge (NS).

number of solid or liquid forms. Examples of liquid forms are emulsifiable concentrates, flowables and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles. Pellets or granules can be manufactured by extrusion with appropriate carriers and binders.

Wettable powders, flowables, and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

TABLE II

| Compound No. | % Control, 3.57 kg/ha | | | | | | | | |
|---|---|---|---|---|---|---|---|---|---|
| | Pre-emergence | | | Contact-and-burn | | | Post-emergence | | |
| | GR avg. | BL avg. | NS | GR avg. | BL avg. | NS | GR avg. | BL avg. | NS |
| 1. | 33 | 33 | 0 | 20 | 30 | 0 | 33 | 17 | 0 |
| 2. | 33 | 0 | 0 | 20 | 20 | 0 | 3 | 7 | 0 |
| 3. | 100 | 100 | 0 | 50 | 50 | 80 | 93 | 90 | 80 |
| 4. | 37 | 62 | 0 | 20 | 20 | 0 | 0 | 3 | 0 |
| 5. | 100 | 100 | 80 | 50 | 50 | 30 | 97 | 97 | 90 |
| 6. | 97 | 100 | 20 | 30 | 30 | 5 | 13 | 10 | 0 |
| 7. | 27 | 40 | 0 | 0 | 10 | 0 | 0 | 0 | 0 |
| 8. | 0 | 7 | 0 | 10 | 20 | 10 | 0 | 57 | 0 |
| 9. | 73 | 100 | 70 | 80 | 80 | 70 | 53 | 65 | 70 |
| 10. | 0 | 10 | 0 | 0 | 40 | 0 | 0 | 33 | 0 |
| 11. | 93 | 100 | 30 | 85 | 80 | 50 | 83 | 95 | 80 |
| 12. | 100 | 100 | 80 | 85 | 80 | 85 | 93 | 92 | 80 |
| 13. | 83 | 96 | 5 | 50 | 70 | 10 | 23 | 73 | 0 |
| 14. | 100 | 100 | 80 | 85 | 85 | 30 | 76 | 86 | 60 |
| 15. | 100 | 100 | 98 | 85 | 85 | 75 | 91 | 93 | 90 |
| 16. | 38 | 31 | 0 | 20 | 60 | 0 | 6 | 30 | 0 |
| 17. | 100 | 98 | 40 | 70 | 60 | 30 | 75 | 68 | 40 |
| 18. | 100 | 100 | 20 | 70 | 70 | 50 | 90 | 71 | 40 |
| 19. | 96 | 86 | 5 | 60 | 70 | 50 | 61 | 71 | 20 |
| 20. | 76 | 50 | 0 | 70 | 60 | 20 | 66 | 40 | 0 |
| 21. | 95 | 73 | 0 | 20 | 40 | 0 | 10 | 36 | 0 |
| 22. | 100 | 100 | 10 | 70 | 85 | 50 | 83 | 91 | 70 |
| 23. | 100 | 100 | 60 | 70 | 70 | 80 | 70 | 71 | 75 |
| 24. | 86 | 100 | 20 | 75 | 85 | 75 | 75 | 88 | 80 |
| 25. | 92 | 87 | 65 | 30 | 40 | 40 | 85 | 93 | 70 |
| 26. | 95 | 98 | 90 | 50 | 50 | 50 | 93 | 95 | 75 |
| 27. | 71 | 100 | 70 | 70 | 75 | 65 | 83 | 80 | 80 |

In practice, a pure compound can be used as an herbicide. However, in general, the compounds are first formulated with one or more inert carriers or diluents suitable for herbicidal use, before being applied.

The compositions or formulations, including a compound as described herein, may exist in any one of a Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are generally also added.

The compositions may also be used in the form of microcapsules. Microcapsules consist of fully enclosed or encapsulated droplets or granules containing the active compound, enclosed within an inert porous membrane, so as to permit escape of the encapsulated material into the surrounding medium or environment at a controlled rate.

Useful encapsulating materials include natural and synthetic rubbers or latexes, cellulosic materials, styrenebutadiene copolymers, polyacrylonitriles, polyacrylates, polyesters, polyamides, polyurethanes and starch xanthates.

It is possible to use highly concentrated liquid compositions containing up to about 95% by weight of the active compound, or even the active compound alone for those compounds which are liquids, when applying the compound in the form of a finely divided liquid by use of various atomizing equipment, for example by airplane crop-spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: Wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the activity of the compound and/or composition and the nature of the seeds and plants to be controlled and will vary from about 0.05 to about 50 pounds per acre (about 0.06 to about 56 kg/ha).

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray spray dusters, or applied from airplanes as mists or sprays. When applied in the latter method, they may be effective in very low dosages. To modify or control growth of germinating seeds or emerging seedlings, liquid compositions may be applied to the soil with conventional methods and may be distributed in the soil to a depth of one-half inch below the soil surface. The compositions need not be admixed with the soil particles, but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | |
|---|---|
| Oil | |
| Ingredient | Weight % |
| Active Compound | 11 |
| Oil solvent-heavy aromatic naphtha | 99 |
| Total | 100 |
| Emulsifiable Concentrate | |
| Active Compound | 50 |
| Kerosene | 45 |
| Emulsifying agent (mixture of long chain ethoxylated polyethers with long chain sulfonate) | 5 |
| Total | 100 |
| Emulsifiable Concentrate | |
| Active Compound | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Active Compound | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| TOTAL | 100.0 | 100.0 | 100.0 |

The compositions of the invention may comprise, in addition to one or more compounds of the invention, one or more compounds not of the invention but which possess biological activity. Compounds not of this invention may be other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus. Accordingly, in yet a still further embodiment, the invention provides an herbicidal composition comprising a mixture of at least one herbicidal compound of formula (I) as hereinbefore defined with at least one other herbicide.

The other herbicide may be any herbicide not having the formula (I). It will generally be an herbicide having a complementary action in the particular application.

Examples of useful complementary herbicides include:

A. Benzo-2,1,3-thiodiazin-4-one-2,2-dioxides such as 3-isopropylbenzo-2,1,3-thiadiazin-4-one-2,2-dioxide (bentazone);

B. hormone herbicides, particularly the phenoxy alkanoic acids such as 4-chloro-2-methylphenoxyacetic acid (MCPA), S-ethyl 4-chloro-0-tolyloxy thioacetate (MCPA-thioethyl), 2-(2,4-dichlorophenoxy) propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy) propionic acid (mecoprop), 3,5,6-trichloro-2-pyridyloxyacetic acid (trichlopyr), 4-amino-3,5-dichloro-6-fluoro-2-pyridyloxyacetic acid (fluroxypyr), 3,6-dichloropyridine-2-carboxylic acid (clopyralid), and their derivatives (e.g. salts, esters and amides);

C. 1,3-dimethylpyrazole derivatives such as 2-[4-(2,4-dichlorobenzoyl) 1,3-dimethylpyrazol-5-yloxy] acetophenone (pyrazoxyfen), 4-(2,4-dichlorobenzoyl)1,3-dimethylpyrazol-5-yltoluene sulfonate (pyrazolate) and 2-[4-(2,4-dichloro-m-toluolyl)-1,3-dimethylpyrazol-5-yloxy]-4'-methylacetophenone (benzofenap);

D. Dinitrophenols and their derivatives (e.g. acetates such as 2-methyl-4,6-dinitrophenol (DNOC), 2-t-butyl-4,6-dinitrophenol (dinoterb), 2-sec.-butyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin), N-ethyl-N-(2-methylallyl)-2,6-dinitro-4-trifluoromethylaniline (ethalfluralin), N-(1-ethylpropyl)-2,6-dinitro-3,4-xylidine (pendimethalin); and 3,5-dinitro-N⁴, N⁴-dipropylsulphanilamide (oryzalin);

F. arylurea herbicides such as N'-(3,4-dichlorophenyl)-N,N-dimethylurea (diuron), N,N-dimethyl-N'-[3-(trifluoromethyl) phenyl]urea (flumeturon), 3-(3-chloro-4-methoxyphenyl)-1,1-dimethylurea (metoxuron), 1-butyl-3-(3,4-dichlorophenyl)-1methylurea (neburon), 3-(4-isopropylphenyl)-1,1-dimethylurea (isoproturon), 3-(3-chloro-p-tolyl)-1,1-dimethylurea (chlorotoluron), 3-[4-(4-chlorophenoxy) phenyl]-1,1-dimethylurea (chloroxuron), 3-(3,4-dichlorophenyl)-1-methylurea (linuron), 3-(4-chlorophenyl)-1-methoxy-1-methylurea (monolinuron), 3-(4bromo-4-chlorophenyl)-1-methoxy-1-methylurea (chlorobromuron), 1-(1-methyl-1-phenylethyl)-3-p-tolylurea (daimuron), and 1-benzothiazol-2-yl-1,3-dimethylurea (methabenzthiazuron);

G. phenylcarbamoyloxyphenylcarbamates such as 3-[methoxycarbonylamino]phenyl (3-methylphenyl)-carbamate (phenmedipham) and 3-[ethoxycarbonylamino]-phenyl phenylcarbamate (desmedipham);

H. 2-phenylpyridazin-3-ones such as 5-amino-4-chloro-2-phenylpyridazin-3-one (chloridazon), and 4-chloro-5-methylamino-2-(α,α,α-trifluoro-m-tolyl) pyridazin-3(2H)-one (norflurazon);

I. uracil herbicides such as 3-cyclohexyl-5,6-trimethyleneuracil (lenacil), 5-bromo-3-sec.-butyl-6-methyluracil (bromacil) and 3-t-butyl-5-chloro-6-methyl-uracil (terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine), 2-azido-4-(i-propylamino)-6-methylthio-1,3,5-triazine (aziprotryne), 2-(4-chloro-6-ethylamino-1,3,5-triazin-2-ylamino)-2-methylpropionitrile (cyanazine), N², N⁴-di-isopropyl-6-methylthio-1,3,5-triazine-2,4-diamine (prometryn), N²-(1,2-dimethylpropyl)N⁴-ethyl-6-methylthio-1,3,5-triazine-2,4-diamine (dimethametryn), N²,N⁴-diethyl-6-methylthio-1,3,5-triazine-2,4-diamine (simetryne), and N²-tert.-butyl-N⁴-ethyl-6-methylthio-1,3,5-triazine-2,4-diamine (terbutryn);

K. phosphorothioate herbicides such as S-2-methyl-piperidinocarbonyl-methyl O,O,-dipropyl phosphorodithioate (piperophos), S-2-benzenesulphonamidoethyl O,O-diisopropyl phosphonodithioate (bensulide), and O-ethyl O-6-nitro-m-tolyl sec.-butylphosphoramidothioate (butamifos);

L. thiolcarbamate herbicides such as S-ethyl N-cyclohexyl-N-ethyl thiocarbamate (cycloate), S-propyl dipropyl-thiocarbamate (vernolate), S-ethyl-azepine-1-carbothioate (molinate), S-4-chlorobenzyl diethylthiocarbamate (thiobencarb), S-ethyl di-isobutyl-thiocarbamate (butylate)*, S-ethyl di-isopropylthiocarbamate (EPTC)*, S-2,3,3-trichloroallyl di-isopropyl thiocarbamate (triallate), S-2,3-dichloroallyl di-isopropyl thiocarbamate (diallate), S-benzyl 1,2-dimethylpropyl (ethyl) thiocarbamate (esprocarb), S-benzyl di(sec.-butyl) thiocarbamate (tiocarbazil), 6-chloro-3-phenylpyridazin-4-yl S-octyl thiocarbamate (pyridate), and S-1-methyl1-phenylethylpiperidine-1-carbothioate (dimepiperate);

M. 1,2,4-triazin-5-one herbicides such as 4-amino-4,5-dihydro-3-methyl-6-phenyl-1,2,4-triazine-5-one (metamitron) and 4-amino-6-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as 2-chloro-2',6'-diethyl-N-(2-propoxyethyl)acetanilide (pretilachlor), N-butoxymethyl-2-chloro-2,,6,-diethylacetanilide (butachlor), the corresponding N-methoxy compound (alachlor), the corresponding N-i-propyl compound (propachlor), 3',4'- dichloropropionanilide (propanil), 2-chloro-N-[pyrazol-1-ylmethyl]acet-2'-6'xylidide(metazachlor), 2-chloro-6'-ethyl-N-(2-methoxy-1-methylethyl) acetotoluidide (metolachlor), 2-chloro-N-ethoxymethyl-6'-ethylacetotoluidide (acetochlor), and 2-chloro-N-(2-methoxyethyl)acet-2',6'-xylidide (dimethachlor);

P. dihalobenzonitrile herbicides such as 2,6-dichlorobenzonitrile (dichlobenil), 3,5-dibromo-4-hydroxy-benzonitrile (bromoxynil) and 3,5-diiodo-4-hydroxy-benzonitrile (ioxynil);

Q. haloalkanoic herbicides such as 2,2-dichloropropionic acid (dalapon), trichloroacetic acid (TCA) and salts thereof;

R. diphenylether herbicides such as ethyl 2-[5-(2-chloro-trifluoro-p-tolyloxy)-2-nitrobenzoyl]oxy propionate (lactofen), D-[5-(2-chloro-α,α,α-trifuoro-p-tolyl)-2-nitrobenzoyl] gycolic acid (fluroglycofen) or salts or esters thereof, 2,4-dichlorophenyl-4-nitrophenyl ether (nitrofen), methyl-(2,4- dichlorophenoxy)-2-nitrobenzoate (bifenox), 2-nitro-5-(2-chloro-4-trifluoromethyl-phenoxy) benzoic acid (acifluorfen) and salts and esters thereof, 2-chloro-4-trifluoromethylphenyl 3-ethoxy-4-nitrophenyl ether (oxyfluorfen) and 5-[2-chloro-4-(trifluoromethyl)phenoxy]-N-(methylsulfonyl)-2-nitrobenzamide (fomesafen); 2,4,6-trichlorophenyl 4-nitrophenyl ether (chlornitrofen) and 5-(2,4-dichlorophenoxy)-2-nitroanisole (chlomethoxyfen);

S. phenoxyphenoxypropionate herbicides such as (RS)-2-[4-(2,4-dichlorophenoxy) phenoxy] propionic acid (diclofop) and esters thereof such as the methyl ester, 2-[4-(5-trifluoromethyl)-2-(pyridinyl)oxy] phenoxypropanoic acid (fluazifop) and esters thereof, 2-[4-(3-chloro-5-trifluoromethyl)-2-pyridinyl)oxy] phenoxypropanoic acid (haloxyfop) and esters thereof, 2-[4-(6-chloro-2-quinoxalinyl)oxy] phenoxypropanoic acid (quizalofop) and esters thereof and (±)-2-[4-(6-chlorobenzoxazol-2-yloxy)phenoxy] propionic acid (fenoxaprop) and esters thereof such as the ethyl ester;

T. cyclohexanedione herbicides such as 2,2-dimethyl-4,6-dioxo-5-[1-(2-propenyloxyimino)butyl] cyclohexane carboxylic acid (alloxydim) and salts thereof, 2-(1-ethoxyimino) butyl-5-[2-(ethylthio)-propyl]-3-hydroxy-2-cyclohexan1-one (sethoxydim), 2-(1-ethoxyimino)butyl-3-hydroxy-5-thian3-ylcyclohex-2-enone (cycloxydim), 2-[1(ethoxyimino)propyl]-3-hydroxy-5-mesityl-cyclohex-2-enone (tralkoxydim), and (±)-2-(E)-1-[(E)-3-chloroallyloximino] propyl-5-[2-(ethylthio)propyl]3-hydroxycyclohex-2-enone (clethodim);

U. sulfonyl urea herbicides such as 2-chloro-N (4-methoxy-6-methyl-1,3,5-triazin-2-yl)-aminocarbonyl) benzenesulphonamide (chlorosulfuron), methyl 2-

[[[(4,6-dimethyl-2-pyrimidinyl)amino]-carbonyl-]amino]-sulphonylbenzoic acid (sulfometuron), 2-[[(3-(4-methoxy-6-methyl-1,3,5-triazin-2-yl)carbonyl-]amino)-sulphonyl)benzoic acid (metsulfuron) and esters thereof; -(4,6-dimethoxypyrimidin-2-ylcarbamoyl-suphamoyl)-O-toluic acid (benzsulfuron) and esters thereof such as the ester thereof methyl, 3-[3-(4-methoxy-6-methyl-1,3,5-triazin-2-yl)ureido- sulphonyl]-thiophene-2-carboxylate (DPX-M6313), 2-(4-chloro-6-methoxy pyrimidin-2-yl carbamoylsulphamoyl benzoic acid (chlorimuron) and esters such as the ethyl ester thereof, 2-(4,6-dimethoxypyrimidin-2-ylcarbamoylsulphamoyl)-N,N-dimethyl-nicotinamide, 2-[4,6-bis(difluoromethoxy)pyrimidin-2-ylcarbamoylsulphamoyl] benzoic acid (pirimisulfuron) and esters such as the methyl ester thereof, 2-[3-(4-methoxy-6-methyl-1,3,5-triazin-zyl)-3-methylureidosulphonyl] benzoic acid esters such as the methyl ester thereof (DPX-LS300) and 5-(4,6-dimethoxypyrimidin-2-ylcarbamoylsulphamoyl)-1-methylpyrazole-4-carboxylic acid (pyrazosulfuron);

V. imidazolidinone herbicides such as 2-(4,5-dihydro-4-isopropyl-4-methyl-5-oxoimidazol-2-yl) quinoline-3-carboxylic acid (imazaquin), methyl 6-(4-isopropyl-4-methyl-5-oxo-2-imidazolin-2-yl)-m-toluate and p-toluate isomer (imazamethabenz), 2-(4-isopropyl-4-methyl-5-oxo-2-imidazolin-2-yl) nicotinic acid (imazapyr) and isopropylammonium salts thereof, (RS)-5-ethyl-2-(4-isopropyl-4-methyl-5-oxo-2-imidazolin-2-yl) nicotinic acid (imazethapyr);

W. arylanilide herbicides such as benzoyl-N-(3-chloro-4-fluorophenyl)-L-alanine (flamprop) and esters thereof, ethyl N-benzoyl-N-(3,4-dichlorophenyl)-DL-alaninate (benzoylprop-ethyl), N-(2,4-difluorophenyl)-2-(3-trifluoromethyl)phenoxy-3-pyridinecarboxamide (diflufenican);

X. amino acid herbicides such as N-(phosphonomethyl)-glycine (glyphosate) and DL-homoalanin-4-yl (methyl)phosphinic acid (gluyfosinate) and their salts and esters, trimethylsulfonium N-(phosphonomethyl)-glycine (sulphosate), and bilanafos;

Y. organoarsenical herbicides such as monosodium methanearsonate (MSMA);

Z. herbicidal amide derivative such as (RS)-N,N-diethyl-2-(1-naphthyloxypropionamide) (napropamide), 3,5-dichloro-N-(1,1-dimethylpropynyl)benzamide (propyzamide), (R)-1-(ethylcarbamoyl)ethyl carbanilate (carbetamide), N-benzyl-N-isopropylpivalamide (tebutam), (RS)-2-bromo-N-(α,α-dimethyl-benzyl)-3,3-dimethylbutyramide (bromobutide), N-[3-(1-ethyl-1-methylpropyl)-isoxazol-5-yl] 2,6-dimethoxybenzamide (isoxaben), N-phenyl-2-(2-naphthyloxy) propionamide (naproanilide), N,N-dimethyl-diphenylacetamide (diphenamid), and N-(1-naphthyl)phthalamic acid (naptalam);

AA. miscellaneous herbicides including 2-ethoxy-2,3-dihydro-3,3-dimethylbenzofuran methanesulfonate (ethofumesate), 7-oxabicyclo (2 2.1)heptane,1-methyl-4-(1-methylethyl)-2-(2-methylphenylmethoxy)-exo (cinmethylin), 1,2-dimethyl-3,5-diphenylpyrazolium ion (difenzoquat) and salts thereof such as the methyl sulfate salt, 2-(2-chlorobenzyl)-4,4-dimethyl-1,2-oxazoldin-3-one (clomazone), 5-tert.-butyl-3-(2,4-dichloro-5-isopropoxyphenyl)-1,3,4-oxadiazol-2(3H)-one (oxadiazon), 3,5-dibromo-4-hydroxy benzaldehyde 2,4-dinitrophenyloxime (bromofenoxim), 4-chlorobut-2-ynyl-3-chlorocarbanilate (barban), (RS)-2-(3,5-dichlorophenyl)-2-(2,2,2-trichloroethyl)oxirane (tridiphane), (3RS,4RS;3RS,4SR)-3-chloro-4-chloromethyl-1-α,α,α-trifluro-m-tolyl-2-pyrrolidone (in the ratio 3:1) (flurochloridone), dichloroquinoline 8-carboxylic acid (quinchlorac) and 2-(1,3-benzothiazol-2-yl-oxy)-N-methylacetanilide (mefanacet);

BB. examples of useful contact herbicides include bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat).

* These compounds are preferably employed in combination with a safener such as 2,2-dichloro-N,N-di-2-propenylacetamide (dichlormid).

What is claimed is:

1. A compound having the formula

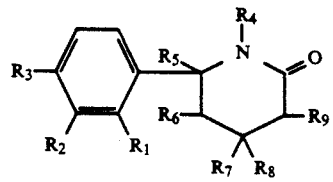

in which:

$R_1$ is hydrogen or fluoro;

$R_2$ is halo, trihalomethyl, pentahaloethyl, mono- or difluoromethyl, di-, tri- or tetrafluoroethyl, $C_1$-$C_2$ fluoroalkylthio, $C_1$-$C_2$ fluoroalkoxy, methylthio, methylsulfonyl, halomethylsulfonyl, $C_1$-$C_2$ alkyl or methoxy;

$R_3$ is hydrogen or halo;

$R_4$ is hydrogen, $C_1$-$C_4$ alkyl; $C_2$-$C_4$ alkenyl; $C_2$-$C_4$ alkynyl; $C_1$-$C_4$ haloalkyl; $C_2$-$C_4$ haloalkenyl; $C_1$-$C_4$ alkoxy; $C_2$-$C_4$ alkoxyalkyl, 3-trifluoromethylphenyl, or —$(CH_2)_nY$;

$R_5$ and $R_6$ are hydrogen, or $R_5$ and $R_6$ together form a bond $R_7$ is $C_1$-$C_4$ alkyl;

$R_8$ and $R_9$ are hydrogen, or $R_8$ and $R_9$ together form a bond;

Y is cyano; 4-chlorophenyl; $C_3$-$C_6$ cycloalkyl, furyl or tetrahydrofuryl optionally substituted by halo or $C_1$-$C_4$ alkyl; or $COR_{10}$ in which $R_{10}$ is hydroxy, $C_1$-$C_5$ alkoxy, $C_1$-$C_5$ alkylthio, —$OCH_2COO(C$-$1$-$C_4$ alkyl) or $NR_{11}R_{12}$ in which $R_{11}$ and $R_{12}$ are independently hydrogen, $C_1$-$C_4$ alkyl, $C_1$-$C_6$ alkoxy, or $C_2$-$C_4$ alkoxyalkyl; and n is 1 or 2.

2. A compound according to claim 1 in which $R_5$ and $R_6$ together form a bond.

3. A compound according to claim 2 in which $R_1$ and $R_3$ are hydrogen.

4. A compound according to claim 1 in which $R_5$ and $R_6$, and $R_8$ and $R_9$, respectively, together form bonds.

5. A compound according to claim 1 in which $R_5$, $R_6$, $R_8$ and $R_9$ are all hydrogen.

6. A compound according to claim 1 in which $R_4$ is $C_1$-$C_4$ alkyl; $C_1$-$C_4$ alkoxy; cyanomethyl $C_2$-$C_4$ alkenyl; $C_2$-$C_4$ haloalkenyl; $C_2$-$C_4$ alkynyl; $C_2$-$C_6$ alkoxyalkyl; or

in which $R_{10}$ is hydroxy, $C_1$-$C_4$ alkoxy, $NH_2$, $N(C_1$-$C_4$ alkyl)$_2$, ($C_3$-$C_6$ cycloalkyl)methyl, furylmethyl or tetrahydrofurylmethyl.

7. A compound according to claim 1 in which $R_1$ and $R_3$ are both hydrogen, $R_4$ is $CH_2CN$ or

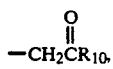

and $R_{10}$ is $C_1-C_4$ alkoxy, hydroxy, or $N(C_1-C_4\ alkyl)_2$.

8. A compound according to claim 1 in which $R_1$, $R_3$, $R_8$ and $R_9$ are all hydrogen, $R_2$ is trifluoromethyl, $R_4$ is $CH_2COOC_2H_5$, $R_5$ and $R_6$ form a bond, and $R_7$ is methyl.

9. A compound according to claim 1 in which $R_1$, $R_3$, $R_8$ and $R_9$ are all hydrogen, $R_2$ is trifluoromethyl, $R_4$ is cyanomethyl, $R_5$ and $R_6$ form a bond, and $R_7$ is methyl.

10. A compound according to claim 1 in which $R_1$, $R_3$, $R_8$ and $R_9$ are all hydrogen, $R_2$ is trifluoromethyl, $R_4$ is 2,2,2-trifluoroethyl, $R_5$ and $R_6$ form a bond, and $R_7$ is methyl.

11. A compound according to claim 1 in which $R_1$, $R_3$, $R_8$ and $R_9$ are all hydrogen, $R_2$ is trifluoromethyl, $R_4$ is $CH_2CON(CH_3)_2$, $R_5$ and $R_6$ form a bond, and $R_7$ is methyl.

12. A compound according to claim 1 in which $R_1$, $R_3$, $R_8$ and $R_9$ are all hydrogen, $R_2$ is trifluoromethyl, $R_4$ is $CH_2COO(t-C_4H_9)$, $R_5$ and $R_6$ form a bond, and $R_7$ is methyl.

13. A compound according to claim 1 in which $R_1$, $R_3$, $R_8$ and $R_9$ are all hydrogen, $R_2$ is trifluoromethyl, $R_4$ is $CH_2COO(i-C_3H_7)$, $R_5$ and $R_6$ form a bond, and $R_7$ is methyl.

14. A compound according to claim 1 in which $R_1$, $R_3$, $R_8$ and $R_9$ are all hydrogen, $R_2$ is trifluoromethyl, $R_4$ is allyl, $R_5$ and $R_6$ form a bond, and $R_7$ is methyl.

15. A compound according to claim 1 in which $R_1$, $R_3$, $R_8$ and $R_9$ are all hydrogen, $R_2$ is trifluoromethyl, $R_4$ is propargyl, $R_5$ and $R_6$ form a bond, and $R_7$ is methyl.

16. A compound according to claim 1 in which $R_1$, $R_3$, $R_8$ and $R_9$ are all hydrogen, $R_2$ is trifluoromethyl, $R_4$ is 2-methoxyethyl, $R_5$ and $R_6$ form a bond, and $R_7$ is methyl.

17. A compound according to claim 1 in which $R_1$, $R_3$, $R_8$ and $R_9$ are all hydrogen, $R_2$ is trifluoromethyl, $R_4$ is n-propyl, $R_5$ and $R_6$ form a bond, and $R_7$ is methyl.

18. A compound according to claim 1 in which $R_1$, $R_3$, $R_8$ and $R_9$ are all hydrogen, $R_2$ is trifluoromethyl, $R_4$ is 3-chloroallyl, $R_5$ and $R_6$ form a bond, and $R_7$ is methyl.

19. A compound according to claim 1 in which $R_1$, $R_3$, $R_8$ and $R_9$ are all hydrogen, $R_2$ is trifluoromethyl, $R_4$ is furyl-2-methyl, $R_5$ and $R_6$ form a bond, and $R_7$ is methyl.

20. A compound according to claim 1 in which $R_1$, $R_3$, $R_8$ and $R_9$ are all hydrogen, $R_2$ is trifluoromethyl, $R_4$ is cyclopropylmethyl, $R_5$ and $R_6$ form a bond, and $R_7$ is methyl.

21. A compound according to claim 1 in which $R_1$, $R_3$, $R_8$ and $R_9$ are all hydrogen, $R_2$ is trifluoromethyl, $R_4$ is methyl, $R_5$ and $R_6$ form a bond, and $R_7$ is methyl.

22. A compound according to claim 1 in which $R_1$, $R_3$, $R_8$ and $R_9$ are all hydrogen, $R_2$ is trifluoromethyl, $R_4$ is ethoxy, $R_5$ and $R_6$ form a bond, and $R_7$ is methyl.

23. A compound according to claim 11 in which $R_1$, $R_3$, $R_5$, $R_6$, $R_8$ and $R_9$ are all hydrogen, $R_2$ is trifluoromethyl, $R_4$ is $CH_2COOC_2H_5$ and $R_7$ is methyl.

24. A compound according to claim 1 in which $R_1$ and $R_3$ are both hydrogen; $R_2$ is trifluoromethyl; $R_5$ and $R_6$, and $R_8$ and $R_9$, respectively, form bonds, $R_4$ is $CH_2COOC_2H_5$ and $R_7$ is methyl.

25. A compound according to claim 1 in which $R_1$ and $R_3$ are both hydrogen; $R_2$ is trifluoromethyl; $R_5$ and $R_6$, and $R_8$ and $R_9$, respectively, form bonds, $R_4$ is $CH_2COO(i-C_3H_7)$ and $R_7$ is methyl.

26. A method of controlling undesirable vegetation comprising applying to said vegetation or the locus thereof a herbicidally effective amount of a compound according to claim 1.

27. A herbicidal composition comprising;
a) a herbicidally effective amount of a compound according to claim 1; and
b) a diluent or carrier suitable for use with herbicides.

* * * * *